United States Patent [19]

Montana et al.

[11] Patent Number: 5,728,712
[45] Date of Patent: Mar. 17, 1998

[54] 3,4-DISUBSTITUTED-PHENYLSULPHONAMIDES AND THEIR THERAPEUTIC USE

[75] Inventors: John Gary Montana; Hazel Joan Dyke; Robert James Maxey; Christopher Lowe, all of Cambridge, United Kingdom

[73] Assignee: Chiroscience Limited, Cambridge, United Kingdom

[21] Appl. No.: 650,672

[22] Filed: May 20, 1996

[30] Foreign Application Priority Data

May 19, 1995 [GB] United Kingdom ............ 9510184
Oct. 6, 1995 [GB] United Kingdom ............ 9520419

[51] Int. Cl.$^6$ ............ C07D 217/08; C07D 217/24; A61K 31/435
[52] U.S. Cl. ............ 514/309; 546/142; 546/153; 546/122; 546/277.1; 514/312; 514/415; 514/418; 514/259; 514/419; 514/416; 514/300; 514/248; 548/491; 548/509; 548/485; 548/492; 548/482; 548/472; 544/287; 544/286; 544/237
[58] Field of Search ............ 546/142, 141; 514/309

[56] References Cited

U.S. PATENT DOCUMENTS

| | | | |
|---|---|---|---|
| 4,289,772 | 9/1981 | Campbell et al. | 424/250 |
| 4,720,580 | 1/1988 | Buzby, Jr. | 564/89 |
| 4,804,673 | 2/1989 | Saito et al. | 514/398 |
| 4,906,640 | 3/1990 | Schöen et al. | 514/300 |
| 4,948,809 | 8/1990 | Witte et al. | 514/538 |
| 5,338,851 | 8/1994 | Huff et al. | 546/141 |
| 5,397,801 | 3/1995 | Wagnon et al. | 514/418 |
| 5,446,065 | 8/1995 | Witte et al. | 514/604 |

FOREIGN PATENT DOCUMENTS

| | | |
|---|---|---|
| 2032570 | 6/1991 | Canada . |
| 2107348 | 7/1993 | Canada . |
| 0326170 | 8/1989 | European Pat. Off. . |
| 0330910 | 9/1989 | European Pat. Off. . |
| 0532177 | 3/1993 | European Pat. Off. . |
| 0606046 | 7/1994 | European Pat. Off. . |
| 2229724 | 10/1990 | United Kingdom . |
| 9402465 | 2/1994 | WIPO . |

OTHER PUBLICATIONS

Athanasiou, C. et al. (1984) "Synthesis of benzenesulfonamide and benzenesulfonohydrazide derivatives. Their effect on Phytopathogenic fungi." Eur. J. Med. Chem. 19(3):281–282.

Dauksas, V., O. Kersulis (1964) "Synthesis of N-substituted 1,4-benzodioxane-6- and veratrol-4-sulfonamides" Chemical Abstracts 61(11):13304.

Buckle, D.R. et al. (1994) "Inhibition of Cyclic Nucleotide Phosphodiesterase by Derivatives of 1,3-Bis (cyclopropylmethyl) xanthine" J. Med. Chem. 37:476–485.

Gaggero, N. et al. (1994) "Oxidation of SR 48117, an antagonist of vasopressin $V_{1a}$ receptors, by biomimetric catalysts based on metalloporphyrin or Schiff-base complexes" Bull Soc. Chim Fr 131:706–712.

Ohshima, E. et al. (1992) "Non-Prostanoid Thromboxane $A_2$ Receptor Antagonists with a Dibenzoxepin Ring System. 1" J. Med. Chem. 35:3394–3402.

Soyka, R. et al. (1994) "6,6-Disubstituted Hex-5-enoic Acid Derivatives as Combined Thromboxane $A_2$ Receptor Antagonists and Synthetase Inhibitors" J. Med. Chem. 37:26–39.

Primary Examiner—Mukund J. Shah
Assistant Examiner—King Lit Wong
Attorney, Agent, or Firm—Saliwanchik, Lloyd & Saliwanchik

[57] ABSTRACT

3,4-Disubstituted-phenylsulphonamides have therapeutic utility via TNF or phosphodiesterase inhibition.

16 Claims, No Drawings

3,4-DISUBSTITUTED-PHENYLSULPHONAMIDES AND THEIR THERAPEUTIC USE

FIELD OF THE INVENTION

The present invention relates to novel sulphonamide compounds and pharmaceutically acceptable salts thereof, processes for their production and formulation and use as pharmaceuticals.

DESCRIPTION OF THE PRIOR ART

International Patent Application WO 94/02465 discloses inhibitors of phosphodiesterase IV and TNF including sulphonamides of formula:

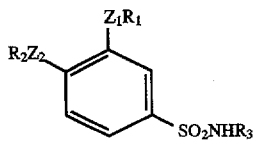

wherein $R^1$ is alkyl, alkenyl, cycloalkyl, cycloalkenyl, cyclothioalkyl, or cyclothioalkenyl; $R^2$ is lower alkyl; $R^3$ is aryl or heteroaryl; $Z^1$ and $Z^2$ are independently oxygen or sulphur. The only sulphonamide exemplified is N-(2-chlorophenyl)-3-cyclopentyloxy-4-methoxybenzenesulphonamide.

U.S. Pat. Nos. 5,283,352 and 4,963,590 disclose compounds of formula

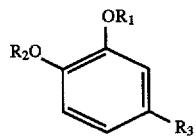

in which $R_3$ may be sulphonamide, as catechol-O-methyl transferase inhibitors.

Phosphodiesterases regulate cyclic AMP concentrations. Phosphodiesterase IV has been demonstrated to be a principal regulator of cyclic AMP in respiratory smooth muscle and inflammatory cells. [See Torphy and Creslinski, *Molecular Pharmacology* 37, 206, (1990); Dent et al *British Journal of Pharmacology*, 90 163p (1990)]. Inhibitors of phosphodiesterase IV have been implicated as being bronchodilators and asthma-prophylactic agents and as agents for inhibiting eosinophil accumulation and the function of eosinophils [see for example Giembycz and Dent, *Clinical and Experimental Allergy* 22 337 (1992)] and for treating other diseases and conditions characterised by, or having an etiology including, morbid eosinophil accumulation. Inhibitors of phosphodiesterase IV are also implicated in treating inflammatory diseases, proliferative skin disease and conditions associated with cerebral metabolic inhibition.

Excessive or unregulated production of Tumour Necrosis Factor (TNF), a serum glycoprotein, has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC, (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as Kupffer and glial cells, have also been implicated in maintenance of the HIV infection. These cells, like T cells, are targets for viral replication and the level of viral replication is dependent upon the activation state of the cells. [See Rosenberg et al, The Immunopathogenesis of HIV Infection, *Advances in Immunology*, Vol. 57, (1989)]. Monokines, such as TNF, have been shown to activate HIV replication in monocytes and/or macrophages [See Poli et al, *Proc. Natl. Acad. Sci.*, 87:782–784, (1990)], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., *Injection and Immunity*, 58(9):2750–54, (1990); and Jafari et al., *Journal of Infectious Diseases*, 164:389–95, (1991). See also Wasan et al., *Antimicrobial Agents and Chemotherapy*, 35, (10):2046–48, (1991); and Luke et al., *Journal of Infectious Diseases*, 162:211–214, (1990)].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

It has been found that novel compounds of formula (i) have ability to treat disease states, for example disease states associated with proteins that mediate cellular activity, for example by inhibiting tumour necrosis factor and/or by inhibiting phosphodiesterase IV. According to the invention, the novel compounds are of formula (i):

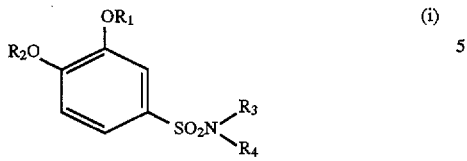

in which $R_1$ represents $C_{1-6}$ alkyl (optionally substituted with halogen, $C_{1-6}$ alkoxy, aryloxy, arylalkyloxy, $C_{1-6}$ alkylamino, arylalkylamino or arylamino), or cycloalkyl (optionally substituted with one or more substituents chosen from amongst halogen, $C_{1-6}$ alkoxy, aryloxy, arylalkyloxy, $C_{1-6}$ alkylamino, arylalkylamino or arylamino);

$R_2$ represents C1-3 alkyl optionally substituted with halogen;

$R_3$ and $R_4$, together with the nitrogen atom to which they are attached, form a 6 or 7 membered heterocyclic ring to which ring is fused a carbocyclic, aryl, heteroaryl or heterocyclic ring, in which either or both rings may optionally be substituted by one or more substituents chosen from aryl, heterocyclo, heteroaryl, $C_{1-6}$ alkyl ( optionally substituted with aryl, heteroaryl, heterocyclo, carbonyl oxygen, hydroxy, $NR_5R_6$, $C_{1-6}$ alkoxy, —CN, $CO_2H$, $CO_2R_7$, $SO_2NR_8R_9$ or $CONR_8R_9$), carbonyl oxygen, $C_{1-6}$ alkoxy, —CN, $CO_2H$, $CO_2R_7$, $SO_2NR_8R_9$, $CONR_8R_9$, halogen, $C_{1-6}$ alkoxy, hydroxy or —$NR_5R_6$; or $R_3$ and $R_4$, together with the nitrogen atom to which they are attached, form a 5 membered heterocyclic or heteroaryl ring to which ring is fused a carbocyclic, aryl, heteroaryl or heterocyclic ring, in which either or both rings may optionally be substituted by one or more substituents chosen from aryl, heterocyclo, heteroaryl, $C_{1-6}$ alkyl ( optionally substituted with aryl, heteroaryl, heterocyclo, carbonyl oxygen, hydroxy, $NR_5R_6$, $C_{1-6}$ alkoxy, —CN, $CO_2H$, $CO_2R_7$, $SO_2NR_8R_9$, or $CONR_8R_9$), arylalkynyl, heteroarylalkynyl, heterocycloalkynyl, carbonyl oxygen, hydroxy, $C_{1-6}$ alkoxy, —CN, $CO_2H$, $CO_2R_7$, $SO_2NR_8R_9$, $CONR_8R_9$, halogen or —$NR_5R_6$, provided that when $NR_3R_4$ represents a dihydroindole ring system the 5 membered ring is not substituted with carbonyl oxygen or hydroxy and the 5 membered ring does not have more than one substituent attached, and also provided that when $NR_3R_4$ represents an imidazole ring, the fused ring does not have more than two substituents attached; $R_5$ and $R_6$, which may be the same or different, each represent H, aryl, heteroaryl, heterocyclo, $C_{1-6}$ alkyl, arylalkyl, heteroarylalkyl, heterocycloalkyl, $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl, provided that when $R_5$ is $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl, $R_6$ is not $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl; or $R_5$, $R_6$ and the nitrogen to which they are attached form a 5 or 6 membered saturated or unsaturated heterocyclic ring (for example morpholine); $R_7$ represents aryl, heteroaryl, heterocyclo, $C_{1-6}$ alkyl, arylalkyl, heteroarylalkyl or heterocycloalkyl; $R_8$ and $R_9$, which may be the same or different, each represent H, aryl, heteroaryl, heterocyclo, $C_{1-6}$ alkyl, arylalkyl, heteroarylalkyl, heterocycloalkyl, or $R_8$, $R_9$ and the nitrogen to which they are attached form a 5 or 6 membered saturated or unsaturated heterocyclic ring (for example morpholine); and pharmaceutically acceptable salts.

DESCRIPTION OF THE INVENTION

Preferred compounds of the invention include those in which, independently or in any combination; $R_1$ is $C_{1-6}$ alkyl (optionally substituted with aryloxy) or cycloalkyl; $R_2$ is methyl optionally substituted with halogen; $R_3$ and $R_4$, together with the nitrogen to which they are attached, form a 6 membered heterocyclic ring to which ring is fused an aryl or heteroaryl ring, in which the first ring may optionally be substituted by one or more substituents chosen from aryl, heteroaryl, $C_{1-6}$ alkyl, carbonyl oxygen, $CO_2H$, $CO_2R_7$ or $CONR_8R_9$ and the fused ring may be optionally substituted with one or more substituents chosen from aryl, heteroaryl, hydroxy, $C_{1-6}$ alkyl, $C_{1-6}$ alkoxy, $CO_2H$, $CO_2R_7$, CN, $CONR_8R_9$, $SO_2NR_8R_9$ or halogen, or $R_3$ and $R_4$, together with the nitrogen atom to which they are attached, form a five membered heterocyclic ring to which ring is fused an aryl or heteroaryl ring, in which the first ring may optionally be substituted by one or more substituents chosen from aryl, heteroaryl, $C_{1-6}$ alkyl, carbonyl oxygen, $CO_2H$, $CO_2R_7$ or $CONR_8R_9$ and the fused ring may be optionally substituted with one or more substituents chosen from aryl, heteroaryl, hydroxy, halogen, $C_{1-6}$ alkyl, $C_{1-6}$ alkoxy, $CO_2H$, $CO_2R_7$, CN, $CONR_8R_9$, arylalkynyl or heteroarylalkynyl; $R_7$ is $C_{1-6}$ alkyl; and $R_8$ and $R_9$, which may be the same or different, are H or $C_{1-6}$ alkyl.

Suitable pharmaceutically acceptable salts are pharmaceutically acceptable base salts and pharmaceutically acceptable acid addition salts. Certain of the compounds of formula (i) which contain an acidic group form base salts. Suitable pharmaceutically acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphate, α-ketoglutarate, α-glycerophosphate and glucose-1-phosphate. The pharmaceutically acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted carbon atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O-group in which the alkyl group is as previously described. Aryloxy means an aryl-O-group in which the aryl group is as defined below. Arylalkyloxy means an aryl-alkyl-O-group. Alkylamino means an alkyl-N-group in which the alkyl group is as previously defined, arylamino means aryl-N- and heteroarylamino means an heteroaryl-N-group (aryl and heteroaryl defined below). Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkyl-group wherein the aryl and alkyl are as described herein. Heteroarylalkyl means a heteroaryl-alkyl group and heterocycloalkyl means a heterocyclo-alkyl group. Alkyl amide includes both monoalkyl and dialkyl amides, in which the alkyl groups (previously described) may be the same or different. Alkylcarbonyl means an alkyl-CO-group in which the alkyl group is as previously described. Arylcarbonyl means an aryl-CO-group in which the aryl group is as previously described. Heteroarylcarbonyl means a heteroaryl-CO-group and heterocyclocarbonyl means a heterocyclo-CO-group. Arylsulphonyl means an aryl-SO$_2$-group in which the aryl group is as previously described. Heteroarylsulphonyl means a heteroaryl-SO$_2$-group and heterocyclosulponyl means a heterocyclo-SO$_2$-group. Alkoxycarbonyl means an alkyloxy-CO-group in wich the alkoxy group is as previously desribed. Alkylsulphonyl means an alkyl-SO$_2$-group in which the alkyl group is as previously described. Carbonyl oxygen means a —CO— group. It will be appreciated that a carbonyl oxygen can not be a substituent on an aryl or heteroaryl ring. Carbocyclic ring means about a 5 to about a 10 membered monocyclic or multicyclic ring system which may saturated or partially unsaturated. Heterocyclic ring means about a 5 to about a 10 membered monocyclic or multicyclic ring system (which may saturated or partially unsaturated) wherein one or more of the atoms in the ring system is an element other than carbon chosen from amongst nitrogen, oxygen or sulphur atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Halogen means fluorine, chlorine, bromine or iodine.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin)has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically acceptable salt thereof.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV- 1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular vital infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The invention further provides a process for the preparation of a compound of formula (i), in which $R_1$–$R_9$ and m-n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, TW Greene. Thus the process for preparing compounds of formula (i) in which $R_3$ contains an —OH comprises of deprotecting (for example by hydrogenolysis or hydrolysis) a compound of formula (i) in which $R_3$ contains an appropriate -OP wherein P represents a suitable protecting group (eg benzyl).

It will be appreciated that where a particular stereoisomer of formula (i) is required, this may be obtained by conventional resolution techniques such as high performance liquid chromatography or the synthetic processes herein described may by performed using the appropriate homochiral starting material.

A process for the preparation of a compound of formula (ia) comprises reaction of an appropriate sulphonyl chloride of formula (ii) with a suitable amine of formula (iii)

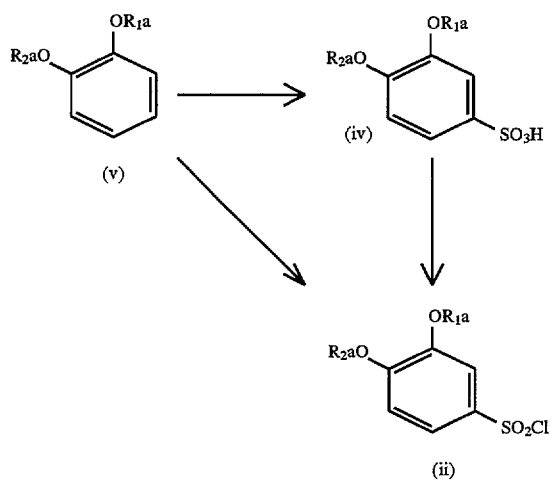

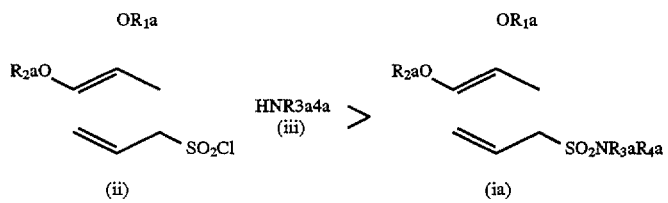

wherein $R_{1a}$ represents $R_1$ as defined in relation to formula (i) or a group convertable to $R_1$ and $R_{2a}$–$R_{4a}$ similarly represent $R_2$–$R_4$ or groups convertable to $R_2$–$R_4$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$. The reaction of a sulphonyl chloride of formula (ii) with a compound of formula (iii) may be carried out under any suitable conditions known to those skilled in the art. When compound (iii) is an amine, favourably the reaction is carried out in the presence of a suitable base, for example an amine such as triethylamine, preferably in an appropriate solvent such as dichloromethane.

Sulphonyl chlorides of formula (ii) are either commercially available or are prepared using standard procedures known to those skilled in the art. For example, a sulphonyl chloride is conveniently prepared from the appropriate sulphonic acid (iv) by treatment with a suitable agent such as thionyl chloride or oxalyl chloride. An appropriate sulphonic acid may be prepared from a compound of formula (v) by sulphonylation using an appropriate sulphonylation agent, for example chlorosulphonic acid. Alternatively, a sulphonyl chloride of formula (ii) may be prepared directly from a compound of formula (v) by using excess chlorosulphonic acid. Compounds of formula (v) are either commercially available or may be prepared by standard procedures known to those skilled in the art.

Compounds of formula (iii) are either commercially available, previously described compounds or are prepared using standard procedures known to those skilled in the art.

In some cases compounds of formula (iii) will be amides (due to the inclusion of a carbonyl group in $R_3$, $R_4$, $R_{3a}$ or $R_{4a}$), and in these cases their reaction with a sulphonyl chloride will require a stronger base, such as sodium hydride, and a polar solvent, favourably N,N-dimethylformamide.

An alternative method for the preparation of compounds of formula (ia) is shown below. This method involves the protection of an appropriate phenol of formula (vi) with a suitable protecting group (for example methanesulphonyl) under standard conditions known to those skilled in the art to provide a compound of formula (vii) and subsequent conversion to a sulphonyl chloride of formula (viii) by sulphonylation or chlorosulphonylation as descibed earlier. Reaction of sulphonyl chloride (viii) with a compound of formula (iii) as descibed earlier provides a compound of formula (ix). Deprotection under standard conditions known to those skilled in the art, followed by alkylation under standard conditions known to those skilled in the art provides a compound of formula (ia).

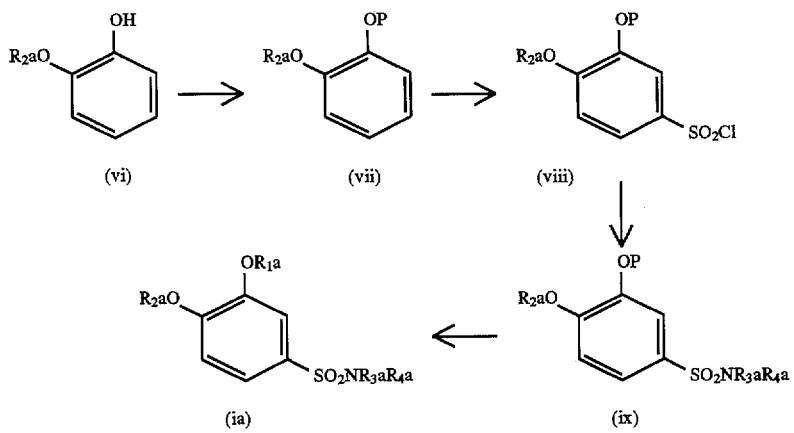

A compound of formula (i) may also be prepared by interconversion of other compounds of formula (i). For example, a compound in which $R_3$ contains a carboxylic acid may be prepared by appropriate hydrolysis of a compound in which $R_3$ contains an alkoxycarbonyl group (for example a methoxycarbonyl group).

A compound of formula (i) or where appropriate a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention provides a pharmaceutical composition comprising a compound of formula (i) or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion tecniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a micro fine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically acceptable salt thereof and/or a pharmaceutically acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically acceptable" encompasses materials suitable for both human and veterinary use.

The following illustrates the invention.

Intermediate 1 3,4-Dimethoxybenzenesulphonamide.

A solution of 3,4-dimethoxybenzenesulphonylchloride (10.0 g) in 1,4-dioxane (80 ml) at ambient temperature under nitrogen was treated with gaseous ammonia until complete conversion had occurred as determined by tlc. The solution was concentrated in vacuo poured into water (400 ml) and extracted with ethyl acetate (2×100 ml). These extracts were washed with water (100 ml) and brine (50 ml) then dried over magnesium sulphate and concentrated in vacuo to give a sticky residue. Trituration with hexane afforded an off-white solid (6.9 g). Crystallisation from ethyl acetate(100 ml)-hexane(65 ml) yielded colourless crystals (4.6 g).

TLC $R_f$ 0.21 (50% ethylacetate/hexane)

mp 134°–135° C.

Intermediate 2 3-Carbomethoxyindole.

A solution of acetyl chloride (5 ml) in methanol (100 ml) was added to indole 3-carboxylic acid (4.5 g) at ambient temperature and stirred whilst monitoring by tlc. The mixture was heated to reflux for 4 hours, allowed to cool to room temperature and concentrated in vacuo. Ethyl acetate (150 ml) and water (250 ml) were added to the residue which was neutralised using sodium bicarbonate. The separated organic phase was washed with water (2×100 ml) and brine (50 ml) then concentrated in vacuo to afford a colourless solid (3.2 g)

TLC $R_f$ 0.53 (50% ethyl acetate/hexane)

mp 146°–148° C.

Intermediate 3 3-Methoxycarbonyl-1,2,3,4-tetrahydroisoquinoline.

Acetyl chloride (0.88 g) was added to methanol (100 ml) with stirring at 0° C. After 10 minutes, 1,2,3,4-tetrahydroisoquinoline-3-carboxylic acid (*J. Am. Chem. Soc.*, 1962, 48, 4487–4494) (2.0 g) was added; the reaction was allowed to warm to room temperature and stirred overnight. DMF (1 ml) was then added and stirring was then continued for a further 24 h. The solvent was removed in vacuo; dichloromethane was added and the solid thus formed was filtered off and partitioned between dichloromethane (50 ml) and saturated aqueous sodium hydrogen carbonate solution (50 ml). The organic phase was dried (magnesium sulphate), filtered, and the filtrate evaporated in vacuo to yield the title compound as a pale yellow oil (1.0 g).

TLC $R_f$ 0.1 (10% ethyl acetate/dichloromethane)

Intermediate 4 2-(Methanesulphonyloxy)methoxybenzene

A solution of 2-methoxyphenol(0.65 ml) in pyridine (20 ml) was cooled to 0° C. under a nitrogen atmosphere. After stirring for 5 minutes, methanesulphonyl chloride (0.62 ml) was added dropwise, and stirring was continued for 15 minutes at 0° C. followed by 1.5 hours at room temperature. The solvent was removed in vacuo and the residue partitioned between water (25 ml) and ethyl acetate (25 ml). The organic phase was dried (magnesium sulphate) and evaporated in vacuo. The crude product was purified by column chromatography on silica, eluting with 20% ethyl acetate in hexane to furnish the title compound (1.76 g) as an oil.

TLC $R_f$ 0.25 (30% ethyl acetate in hexane)

Intermediate 5 3-Methanesulphonyloxy-4-methoxybenzenesulphonyl chloride

A solution of 2-(methanesulphonyloxy)methoxybenzene (0.822 g) in dichloromethane (15 ml) was stirred and cooled to −10° C. under a nitrogen atmosphere. A solution of chlorosulphonic acid (0.27 ml) in dichloromethane (5 ml) was then added dropwise over a period of 1 hour, maintaining the temperature below 0° C. The mixture was stirred for a further 4 hours, allowing the temperature to rise to 10° C. The mixture was evaporated to dryness in vacuo to yield an oil which was suspended in toluene (20 ml) with stirring under a nitrogen atmosphere. Oxalyl chloride (0.36 ml) was added dropwise, followed by the addition of DMF (5 drops). After stirring for 2 hours at room temperature, dichloromethane (15 ml) and oxalyl chloride (0.36 ml) were added and the reaction stirred overnight. The solvent was evaporated in vacuo and the residue was purified by column chromatography on silica, eluting with 60% ethyl acetate in hexane to furnish the title compound (0.99 g) as a white crystalline solid.

TLC $R_f$ 0.4 (60% ethyl acetate in hexane)

Intermediate 6 N-(3-Methanesulphonyloxy-4-methoxybenzenesulphonyl)-1,2-dihydroindole This intermediate was prepared from intermediate 5 and indoline using the procedure of example 1. Purification by column chromatography eluting with dichloromethane yielded the title product as a white solid (1.1 g).

TLC $R_f$ 0.56 (dichloromethane)

mp 133°–134° C.

Intermediate 7 N-(3-Hydroxy-4-methoxybenzenesulphonyl)-1,2-dihydroindole.

A solution of N-(3-methanesulphonyloxy-4-methoxybenzenesulphonyl)-1,2-dihydroindole (1 g) and saturated aqueous sodium hydroxide solution (2 ml) was heated at 85°–90° C. for 2 hours. The solvent was removed in vacuo and the residue partitioned between ethyl acetate (5 ml) and water (10 ml). The aqueous phase was acidified with 2N HCl and extracted with ethyl acetate (2×10 ml). The combined organic phases were dried over magnesium sulphate and concentrated in vacuo to yield a clear oil. Purification by column chromatography eluting with dichloromethane afforded the desired product as a white solid (0.8 g).

TLC $R_f$ 0.69 (10% ethyl acetate/dichloromethane)

mp 139°–140° C.

Intermediate 8 N-(3,4-Dimethoxybenzenesulphonyl)-2-iodobenzamide.

2-Iodobenzoic acid (1.5 g) was suspended in dry dichloromethane (10 ml) at room temperature under an inert atmosphere and 1-(3-dimethylaminopropyl)-3-ethylcarbodiimide hydrochloride (1.2 g) added. 3,4-Dimethoxybenzenesulphonamide (1.3 g) and 4-dimethylaminopyridine (0.75 g) were then added and stirred for 17 hours. The reaction mixture was poured into dichloromethane (100 ml), washed with dilute hydrochloric acid (60 ml), water (60 ml) and saturated brine (40 ml) then dried over anhydrous magnesium sulphate, filtered and evaporated in vacuo to yield a foam (2.4 g). This crude material was purified by column chromatography eluting with 20–100% ethyl acetate-hexane to afford a white solid (1.36 g).

TLC $R_f$ 0.35 (50% ethyl acetate/hexane)

mp 135°–137° C.

EXAMPLE 1

N-(3,4-Dimethoxybenzenesulphonyl)-1,2,3,4-tetrahydroquinoline 1,2,3,4-Tetrahydroquinoline (0.29 ml) was added to a suspension of 3,4-dimethoxybenzene sulphonyl chloride (0.50 g) in dichloromethane (15 ml) at room temperature. Triethylamine (0.44 ml) was added and the resulting mixture stirred for 24 hours at room temperature. The reaction mixture was then diluted with dichloromethane (20 ml) and washed successively with saturated aqueous sodium hydrogen carbonate solution (10 ml), 2N hydrochloric acid (10 ml) and saturated aqueous sodium chloride solution (10 ml). Drying over magnesium sulphate and concentration in vacuo provided a yellow oil. Purification by column chromatography eluting with 30% ethyl acetate in hexane provided the title compound as a colourless oil (0.60 g) which solidified on standing.

TLC $R_f$ 0.30 (30% ethyl acetate in hexane)

Mp 84°–85° C.

The following compounds were prepared using the above procedure from the appropriate starting material.

EXAMPLE 2

N-(3,4-Dimethoxybenzenesulphonyl)-1,2,3,4-tetrahydroisoquinoline

TLC $R_f$ 0.30 (30% ethyl acetate in hexane)

Mp 125°–127° C.

EXAMPLE 3

N-(3,4-Dimethoxybenzenesulphonyl)indoline

Purification by column chromatography eluting with 60% ethyl acetate in hexane provided the title compound as an off white solid which was recrystallised from ethyl acetate/hexane (0.17 g).

TLC $R_f$ 0.55 (60% ethyl acetate in hexane)

Mp 110°–111° C.

EXAMPLE 4

N-(3,4-Dimethoxybenzenesulphonyl)-3-phenyl-1,2,3,4-tetrahydroisoquinoline.

Prepared from 3-phenyl-1,2,3,4-tetrahydroisoquinoline(*J. Heterocyclic Chem.*, 1983, 20, 121–128). Purification by column chromatography eluting with 40–50% ethyl acetate in hexane afforded the product as a white solid (66 mg).

TLC $R_f$ 0.5 (50% ethyl aceatate/hexane)

mp 138°–138.5° C.

EXAMPLE 5

N-(3,4-Dimethoxybenzenesulphonyl)isatin.

Recrystallization from dichloromethane furnished the product as a yellow solid (262 mg).

TLC $R_f$ 0.45 (50% ethyl acetate/hexane)

mp 222°–223° C.

EXAMPLE 6

N-(3,4-Dimethoxybenzenesulphonyl)-3-methoxycarbonyl-1,2,3,4-tetrahydroisoquinoline.

Prepared from 3-methoxycarbonyl-1,2,3,4-tetrahydroisoquinoline. Purification by column chromatography gave the title compound as a colourless gum (0.80 g).

TLC $R_f$ 0.75 (dichloromethane)

FTIR (KBr) 2953, 1745, 1588, 1509, 1455, 1405, 1332, 1263, 1157, 1021 cm$^{-1}$.

EXAMPLE 7

N-(3,4-Dimethoxybenzenelsulphonyl)indole

Pyridinium chlorochromate (0.34 g) and celite (0.75 g), which had been ground together, were added to a solution of N-(3,4-dimethoxybenzenesulphonyl)indoline (0.10 g) in dry toluene (5 ml), and the resulting mixture was heated at reflux under nitrogen for 4 hours. Further toluene (10 ml) was added and the reaction stirred overnight at room temperature. The mixture was then diluted with diethyl ether (15 ml) and filtered through a pad of celite and magnesium sulphate. The pad was washed with diethyl ether (2×15 ml) and the organic solution concentrated in vacuo to give a yellow oil.

Purification by column chromatography eluting with 50% ethyl acetate in hexane provided the title compound as a white solid (0.03 g).

TLC R*f* 0.60 (60% ethyl acetate in hexane)
Mp 104°–105° C.

EXAMPLE 8

N-(3,4-Dimethoxybenzenesulphonyl)-2,3-dihydro-4-quinolinone

The procedure of example 7 was used. Purification by column chromatography eluting with 55% ethyl acetate in hexane provided the title compound as a white solid which was recrystallized from ethyl acetate/hexane (0.026 g).

TLC R*f* 0.4 (50% ethyl acetate/hexane).

EXAMPLE 9

N-[3-(Phenoxypropoxy)-4-methoxybenzenesulphonyl]-1,2-dihydroindole.

A solution of N-(3-hydroxy-4-methoxybenzenesulphonyl)- 1,2-dihydroindole (0.2 g) and 3-phenoxypropylbromide (0.15 g) in N,N-dimethylformamide (20 ml) was treated with cesium carbonate (0.3 g) and heated at 75° C. overnight. The solvent was removed in vacuo and the residue partitioned between dichloromethane (30 ml) and water (15 ml). The organic phase was washed with brine (15 ml) then dried over magnesium sulphate and concentrated in vacuo. The residue was purified using column chromatography eluting with dichloromethane to yield the title compound as a white solid (0.25 g).

TLC R*f* 0.52 (dichloromethane)
mp 112°–113° C.

EXAMPLE 10

N-(3,4-Dimethoxybenzenesulphonyl)-3-phenylisocarbostyril.

A solution of 3-phenylisocarbostyril (0.1 g) in N,N-dimethylformamide (2 ml) was cooled to 0° C. under an inert atmosphere. Sodium hydride (0.019 g) was added and the resulting mixture stirred at 0° C. for 5 minutes. 3,4-Dimethoxybenzenesulphonylchloride (0.107 g) was added over a 3 minute period, with continued stirring at 0° C. for a further 15 minutes. The reaction mixture was warmed to room temperature and stirred for 24 hours. The DMF was evaporated under high vacuum and the residue partitioned between ethyl acetate (2×12 ml) and water (12 ml). The combined organic phases were dried over magnesium sulphate and concentrated in vacuo to yield a yellow oil. Purification using column chromatography eluting with 50% ethyl acetate in hexane yielded an oil which was crystallized from ethyl acetate/hexane to furnish the title compound as white crystals (0.089 g).

TLC R*f* 0.5 (50% ethyl acetate/hexane)
mp 138°–139° C.

The following compounds were prepared using the above procedure from the appropriate starting materials.

EXAMPLE 11

N-(3,4-Dimethoxybenzenesulphonyl)benzimidazole.

Purification by column chromatography eluting with 40% ethyl acetate in hexane afforded the product as a white solid (0.47 g).

TLC R*f* 0.25 (40% ethyl acetate/hexane)
mp 110°–111° C.

EXAMPLE 12

N-(3,4-Dimethoxybenzenesulphonyl)isocarbostyril.

Prepared from isocarbostyril. Purification by column chromatography eluting with dichloromethane afforded the product as a colourless solid (0.17 g).

TLC R*f* 0.11 (50% dichloromethane/hexane)
mp 170°–171° C.

EXAMPLE 13

N-(3,4-Dimethoxybenzenesulphonyl)-4-phenylisocarbostyril.

Prepared from 4-phenylisocarbostyril(*Liebigs Ann. Chem.*, 1981, 52–57). Purification by column chromatography eluting with 50% ethyl acetate in hexane afforded the product as a colourless solid (0.11 g).

TLC R*f* 0.40 (50% ethyl acetate/hexane)
mp 160°–161° C.

EXAMPLE 14

3-(3,4-Dimethoxybenzenesulphonyl)-2-phenyl-4-quinazolinone.

Prepared from 2-phenyl-4-quinazolinone (*Synth. Commun.*, 1981, 35). Purification by column chromatography eluting with 3% ethyl acetate in dichloromethane afforded the product as a colourless solid (0.07 g).

TLC R*f* 0.66 (3% ethyl acetate/dichloromethane)
mp 96°–98° C.

EXAMPLE 15

3-(3,4-Dimethoxybenzenesulphonyl)-4-phenyl-2-quinazolinone.

Prepared from 4-phenyl-2-quinazolinone (*J. Org. Chem.*, 1962, 27, 4424–4426 and *Chem. Pharm. Bull.*, 1978, 26(6), 1633–1651). Purification by column chromatography eluting with 50% ethyl acetate in hexane afforded the product as a colourless solid (0.14 g).

TLC R*f* 0.31 (50% ethyl acetate/hexane)
mp 163°–165° C.

EXAMPLE 16

3-Carbomethoxy-N-(3,4-dimethoxybenzenesulphonyl) indole.

Prepared from 3-carbomethoxyindole. Purification by column chromatography eluting with 50% ethyl acetate in hexane furnished the title compound as a colourless solid (1.28 g).

TLC R*f* 0.45 (50% ethyl acetate/hexane)
mp 47°–49° C.

EXAMPLE 17

N-(3,4-Dimethoxybenzenesulphonyl)-1-oxo-3-phenyl-2,3-dihydro(1H)-isoindole.

Prepared from 1-oxo-3-phenyl-2,3-dihydro(1H)isoindole (*Chem. Ber.*, 1972, 105, 2933–2954). Purification by column chromatography afforded a white foam (0.077 g).

TLC R$_f$ 0.4 (50% ethyl acetate/hexane)
FTIR; 1729, 1586, 1508, 1265, 1165, 1090 cm$^{-1}$.

EXAMPLE 18

3-Carbomethoxy-N-(3,4-dimethoxybenzenesulphonyl)-1-oxo-1,2-dihydroisoquinoline.

Prepared from 3-carbomethoxy-1-oxo-1,2-dihydroisoquinoline (*J. Org. Chem.*, 1979,44, 1887–1888). Purification by column chromatography afforded an off-white solid (0.13 g).

TLC R$_f$ 0.4 (50% ethyl acetate/hexane).
mp 160°–162° C.

EXAMPLE 19

6-(3,4-Dimethoxybenzenesulphonyl)-7-phenyl-1,6-naphthyridin-5(6H)-one.

Prepared from 7-phenyl-1,6-naphthyridin-5(6H)-one (*J. Chem. Soc. Perkin Trans.* 1, 1972, 705). Purification by column chromatography afforded a cream solid (0.074 g).

TLC R$_f$ 0.45 (75% ethyl acetate/hexane).
mp 114°–115° C.

EXAMPLE 20

3,4-Dihydro-1-(3,4-dimethoxybenzenesulphonyl)-3-methyl-2(1H)-quinazolinone.

Prepared from 3,4-dihydro-3-methyl-2(1H)-quinazolinone. The crude reaction product was suspended in methanol and the insoluble material filtered off to afford a white solid (1.71 g).

TLC R$_f$ 0.12 (50% ethyl acetate/hexane).
mp 191°–192° C.

EXAMPLE 21

6-(3,4-Dimethoxybenzenesulphonyl)-7-methyl-1,6-naphthyridin-5(6H)-one.

Prepared from 7-methyl-1,6-naphthyridin-5(6H)-one (*J. Chem. Soc. Perkin Trans.* 1, 1972, 705) to afford a white solid after crystallisation.

TLC R$_f$ 0.4 (50% ethyl acetate/hexane).
mp 118°–119° C.

EXAMPLE 22

2-(3,4-Dimethoxybenzenesulphonyl)-1(2H)-phthalazinone.

Prepared from 1 (2H)-phthalazinone. Purification by column chromatography eluting with 15% ethyl acetate-dichloromethane afforded a white solid (0.028 g).

TLC R$_f$ 0.57 (15% ethyl acetate/dichloromethane).
mp 177°–178.5° C.

EXAMPLE 23

2-(3,4-Dimethoxybenzenesulphonyl)-4-bromoisoindoline.

A solution of 3,4-dimethoxybenzenesulphonamide(0.9 g) in N,N-dimethylformamide (2 ml) was added to a suspension of sodium hydride (0.34 g) in N,N-dimethylformamide (10 ml) and stirred under nitrogen at ambient temperature for 1 hour. This mixture was heated under reflux for a further hour before allowing to cool to 60° C. and a solution of 2,3-bis(bromomethyl)bromobenzene (1.5 g; Eur. Pat. Appl. EP343560 A2/891129) in N,N-dimethyl formamide (3 ml) added. After heating at 60° C. for an hour the now brown mixture was allowed to cool to room temperature overnight then poured onto ice. Ethyl acetate (2×80 ml) extracts of this mixture were washed with dilute hydrochloric acid (100 ml), aqueous sodium carbonate (100 ml) and brine, dried over magnesium sulphate then concentrated in vacuo to afford a yellow residue (1.2 g). Purification by column chromatography eluting with a 10–40% ethyl acetate in hexane gradient afforded the product as a colourless solid (0.3 g).

TLC R$_f$ 0.48 (50% ethylacetate/hexane)
mp 167°–169° C.

EXAMPLE 24

N-(3,4-Dimethoxybenzenesulphonyl)-3-carboxy-1,2,3,4-tetrahydroisoquinoline.

A solution of N-(3,4-dimethoxybenzenesulphonyl)-3-methoxycarbonyl-1,2,3,4-tetrahydro-isoquinoline(0.5 g) in THF (30 ml) was treated with a saturated aqueous solution of lithium hydroxide (3 ml) at room temperature. After stirring overnight, the solvent was removed in vacuo. The residue was diluted with water (10 ml), washed with ethyl acetate (10 ml) and acidified with 2M hydrochloric acid. The aqueous phase was extracted with ethyl acetate (2×30 ml); these extracts were combined and dried (magnesium sulphate). Evaporation of the solvent in vacuo and recrystallization of the residue from ethyl acetate/hexane afforded the title compound as a whim solid (0.44 g).

TLC R$_f$ 0.26 (10% ethyl acetate/dichloromethane)
mp 191°–193° C.

The following compound was prepared according to the above procedure:

EXAMPLE 25

3-Carboxy-N-(3,4-dimethoxybenzenesulphonyl) indole.

Prepared from 3-carbomethoxy-N-(3,4-dimethoxybenzenesulphonyl)indole. The product was obtained as a white solid (0.75 g).

TLC R$_f$ 0.2 (ethyl acetate)
mp 206°–209° C.

EXAMPLE 26

N-(3,4-Dimethoxybenzenesulphonyl)-3-phenyl-5,6,7,8-tetrahydroisocarbostyril.

A solution of N-(3,4-dimethoxybenzenesulphonyl)-3-phenylisocarbostyril (0.10 g) in 50% ethanol-tetrahydrofuran(50 ml) was treated with platinum oxide (10 mg) and stirred thoroughly at room temperature under an atmosphere of hydrogen. After 7 days the reaction mixture was filtered through Celite and the filtrate evaporated in vacuo. The resultant residue was purified by column chromatography eluting with 33% ethyl acetate-hexane to afford a white solid (0.066 g)

TLC R$_f$ 0.48 (33% ethyl acetate/hexane)
mp 125°–126° C.

EXAMPLE 27

N-(3,4-Dimethoxybenzenesulphonyl)-3,4-dihydrophenylisocarbostyril.

N-(3,4-Dimethoxybenzenesulphonyl)isocarbostyril (300 mg) in tetrahydrofuran (50 ml) was treated with 10% palladium on carbon (30 mg) and stirred thoroughly under an atmosphere of hydrogen. After 2 weeks the reaction mixture was filtered through Celite and the filtrate evaporated in vacuo. The resultant residue was purified by column chromatography eluting with 50% ethyl acetate-hexane to afford a white solid (0.30 g).

TLC $R_f$ 0.09 (50% dichloromethane/hexane)

mp 165°–167° C.

EXAMPLE 28

N-(3,4-Dimethoxybenzenesulphonyl)-4-pyrid-2-ylisocarbostyril.

N-(3,4-Dimethoxybenzenesulphonyl)-2-iodobenzamide (0.94 g) was dissolved in dry N,N-dimethylformamide (7 ml) at room temperature under an inert atmosphere. Triethylamine (0.6 ml) and bis(triphenylphosphine)palladium (II) chloride (0.20 g) were added, and the stirred mixture heated to 90° C. Dropwise addition of a solution of 2-ethynylpyridine (0.90 g) in dry N,N-dimethylformamide(3 ml) gave a black mixture that was continued to be heated at 90° C. for a further 3 hours before allowing to cool to room temperature. 50% Ethyl acetate-diethyl ether (40 ml) was added and the mixture filtered through a pad of silica eluting with ethyl acetate. Evaporation of the filtrate in vacuo yielded a dark residue that was purified by column chromatography eluting with 20–100% ethyl acetate-hexane then 10% methanol-dichloromethane to afford a brown oil (375 mg).

TLC $R_f$ 0.10 (50% ethyl acetate/hexane)

FTIR (film); 1740, 1584, 1510, 1266 cm$^{-1}$.

EXAMPLE 29

2-(3,4-Dimethoxybenzenesulphonyl)-4-(2-pyrid-2-ylethynyl)isoindoline.

2-(3,4-Dimethoxybenzenesulphonyl)-4-bromoisoindoline (0.19 g), triethylamine (0.10 ml), 2-ethynylpyridine(0.06 g) and bis (triphenylphosphine) palladium(II)chloride (10%) in anhydrous N,N-dimethylformamide(2 ml) were stirred together under an inert atmosphere and heated to 90° C. After 20 hours further 2-ethynylpyridine(0.12 g) and palladium catalyst (20%) were added and heating continued for 3 days. The reaction mixture at room temperature was diluted with ethyl acetate, filtered through a pad of silica and the filtrate evaporated in vacuo to yield a yellow residue. Purification by column chromatography, eluting with a 20–100% ethyl acetate in hexane gradient afforded the title compound (25 mg).

TLC $R_f$ 0.15 (50% ethyl acetate/hexane)

FTIR (film)2216, 1582, 1509, 1348, 1263, 1157 cm$^{-1}$.

Assay methods

The assays used to confirm the phosphodiesterase IV inhibitory activity of compounds of formula (I) are standard assay procedures as disclosed by Schilling et al, *Anal. Biochem.* 216 154 (1994), Thompson and Strada, *Adv. Cycl. Nucl. Res.* 8 119 (1979) and Gristwood and Owen, *Br. J. Pharmacol.* 87 91P (1986).

Compounds of formula (I) have exhibited activity at levels consistent with those believed to be useful in treating phosphodiesterase IV related disease states in those assays.

We claim:

1. A compound of the general formula (i)

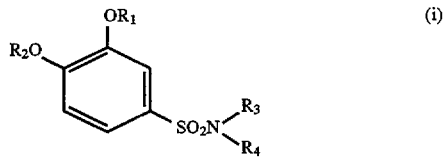

in which $R_1$ represents $C_{1-6}$ alkyl (optionally substituted with halogen, $C_{1-6}$ alkoxy, aryloxy, arylalkyloxy, $C_{1-6}$ alkylamino, arylalkylamino or arylamino), or cycloalkyl, optionally substituted with one or more substituents selected from the group consisting of halogen, $C_{1-6}$ alkoxy, aryloxy, arylalkyloxy, $C_{1-6}$ alkylamino, arylalkylamino and arylamino;

$R_2$ represents C1-3 alkyl optionally substituted with halogen;

$R_3$ and $R_4$, together with the nitrogen atom to which they are attached, form an isoquinolinyl, dehydrogenated isoquinolinyl, isocarbostyril or dehydrogenated isocarbostyril group in which either or both rings may optionally be substituted by one or more substituents selected from the group consisting of aryl, heterocyclo, heteroaryl, $C_{1-6}$ alkyl, optionally substituted with aryl, heteroaryl, heterocyclo, carbonyl oxygen, hydroxy, $NR_5R_6$, $C_{1-6}$ alkoxy, —CN, $CO_2H$, $CO_2R_7$, $SO_2NR_8R_9$ or $CONR_8R_9$, carbonyl oxygen, hydroxy, $C_{1-6}$ alkoxy, —CN, $CO_2H$, $CO_2R_7$, $SO_2NR_8R_9$, $CONR_8R_9$, halogen, $C_{1-6}$ alkoxy, hydroxy and —$NR_5R_6$;

$R_5$ and $R_6$, which may be the same or different, each represent H, aryl, heteroaryl, heterocyclo, $C_{1-6}$ alkyl, arylalkyl, heteroarylalkyl, heterocycloalkyl, $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl, provided that when R5 is $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl, R6 is not $C_{1-6}$ alkylcarbonyl, $C_{1-6}$ alkoxycarbonyl, arylsulphonyl, heteroarylsulphonyl, heterocyclosulphonyl, heteroarylcarbonyl, heterocyclocarbonyl, arylcarbonyl or $C_{1-6}$ alkylsulphonyl; or $R_5$, $R_6$ and the nitrogen to which they are attached form a 5 or 6 membered saturated or unsaturated heterocyclic ring;

$R_7$ represents aryl, heteroaryl, heterocyclo, $C_{1-6}$ alkyl, arylalkyl, heteroarylalkyl or heterocycloalkyl; and $R_8$ and $R_9$, which may be the same or different, each represent H, aryl, heteroaryl, heterocyclo, $C_{1-6}$ alkyl, arylalkyl, heteroarylalkyl, heterocycloalkyl, or $R_8$, $R_9$ and the nitrogen to which they are attached form a 5 or 6 membered saturated or unsaturated heterocyclic ring, and pharmaceutically acceptable salts thereof.

2. The compound of claim 1, wherein $R_1$ is alkyl or cycloalkyl, either being optionally substituted by halogen, alkoxy, aryloxy or arylalkoxy.

3. The compound of claim 2, wherein $NR_3R_4$ is an isoquinolinyl, dehydrogenated isoquinolinyl, isocarbostyril or dehydrogenated isocarbostyril group, in which the nitrogen-containing ring may optionally be substituted by one or more substituents selected from the group consisting of aryl, heteroaryl, carbonyl oxygen, OH, alkoxy, CN, COOH, $CO_2R_7$, $CONR_8R_9$, and alkyl optionally substituted by carbonyl oxygen, OH, alkoxy, CN, COOH, $CO_2R_7$ or $CONR_8R_9$ and the fused 6-membered carbocyclic ring may optionally be substituted by one or more substituents selected from the group consisting of aryl, heteroaryl, carbonyl oxygen, OH, alkoxy, CN, COOH, $CO_2R_7$, $CONR_8R_9$, halogen, $NR_5R_6$ and alkyl optionally substituted by carbonyl oxygen, OH, alkoxy, CN, COOH, $CO_2R_7$ or $CONR_8R_9$; and $R_5$ and $R_6$ are independently selected from the group consisting of H, alkyl, alkylcarbonyl, alkoxycarbonyl, arylsulphonyl, arylcarbonyl and alkylsulphonyl.

4. The compound of claim 1, wherein $R_1$ is alkyl optionally substituted by aryloxy, or cycloalkyl.

5. The compound of claim 1, wherein $R_2$ is methyl optionally substituted by halogen.

6. The compound of claim 1, wherein $NR_3R_4$ is an isoquinolinyl, dehydrogenated isoquinolinyl, isocarbostyril or dehydrogenated isocarbostyril, in which the nitrogen-containing ring being optionally substituted by one or more of aryl, heteroaryl, alkyl, carbonyl oxygen, COOH, $COOR_7$ and $CONR_8R_9$, and the fused 6-membered carbocyclic ring being optionally substituted by one or more of aryl, heteroaryl, OH, alkyl, alkoxy, COOH, $COOR_7$, CN, $CONR_8R_9$, halogen and $SONR_8R_9$.

7. The compound of claim 1, which is

N-(3,4-Dimethoxybenzenesulphonyl)-1,2,3,4-tetrahydroisoquinoline.

8. The compound of claim 1, selected from the group consisting of

N-(3,4-Dimethoxybenzenesulphonyl)-3-phenyl-1,2,3,4-tetrahydro-isoquinoline,

N-(3,4-Dimethoxybenzenesulphonyl)-3-methoxycarbonyl-1,2,3,4-tetrahydroisoquinoline, N-(3,4-Dimethoxybenzenesulphonyl)-3-phenylisocarbostyril, N-(3,4-Dimethoxybenzenesulphonyl)isocarbostyril, N-(3,4-Dimethoxybenzenesulphonyl)-4-phenylisocarbostyril, and N-(3,4-Dimethoxybenzenesulphonyl)-3-carboxy-1,2,3,4-tetrahydro-isoquinoline.

9. The compound of claim 1, selected from the group consisting of

3-Carbomethoxy-N-(3,4-dimethoxybenzenesulphonyl)-1-oxo-1,2-dihydroisoquinoline,

N-(3,4 Dimethoxybenzenesulphonyl)-3-phenyl-5,6,7,8-tetrahydroisocarbostyril,

N-(3,4-Dimethoxybenzenesulphonyl)-3,4-dihydrophenylisocarbostyril, and

N-(3,4-Dimethoxybenzenesulphonyl)-4-pyrid-2-ylisocarbostyril.

10. The compound of claim 1, in the form of an enantiomer or diastereoisomer, or any mixture of either.

11. A pharmaceutical composition comprising a compound according to claim 1 as active ingredient, in combination with a suitable excipient.

12. A method for treating a disease state in a human or animal capable of being modulated by inhibiting production of phosphodiesterase IV, comprising administering to said human or animal suffering from said disease an effective amount of a compound according to claim 1.

13. The method of claim 12, wherein the disease state is a pathological condition associated with a function of phosphodiesterase IV, eosinophil accumulation or a function of the eosinophil.

14. The method of claim 13, wherein the pathological condition is selected from the group consisting of asthma, chronic bronchitis, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic dermatitis, atopic eczema, cerebral senility, multi-infarct dementia, senile dementia, memory impairment associated with Parkinson's disease, depression, cardiac arrest, stroke and intermittent claudication.

15. The method of claim 14, wherein the pathological condition is asthma.

16. The method of claim 12, wherein the disease state is tardive dyskinesia.

* * * * *